US012740721B2

(12) United States Patent
Quek et al.

(10) Patent No.: US 12,740,721 B2
(45) Date of Patent: Sep. 22, 2026

(54) SYSTEMS, DEVICES, AND METHODS FOR DETERMINING BREATH RATE USING AN OPTICAL FLOW SENSING

(71) Applicant: STMICROELECTRONICS INTERNATIONAL N.V., Geneva (CH)

(72) Inventors: Kien Wee Mike Quek, Singapore (SG); Tomohiro Yonemaru, Tokyo (JP); Matteo Maravita, Sai Kung (HK)

(73) Assignee: STMICROELECTRONICS INTERNATIONAL N.V., Geneva (CH)

( * ) Notice: Subject to any disclaimer, the term of this patent is extended or adjusted under 35 U.S.C. 154(b) by 318 days.

(21) Appl. No.: 18/588,993

(22) Filed: Feb. 27, 2024

(65) Prior Publication Data

US 2025/0268487 A1 Aug. 28, 2025

(51) Int. Cl.

| | |
|---|---|
| ***A61B 5/08*** | (2006.01) |
| ***A61B 5/087*** | (2006.01) |
| ***G06T 5/50*** | (2006.01) |
| ***G06T 5/70*** | (2024.01) |
| ***G06T 7/194*** | (2017.01) |
| ***G06V 40/10*** | (2022.01) |

(52) U.S. Cl.

CPC .......... *A61B 5/0816* (2013.01); *A61B 5/0873* (2013.01); *G06T 5/50* (2013.01); *G06T 5/70* (2024.01); *G06T 7/194* (2017.01); *G06V 40/103* (2022.01); *G06T 2207/20224* (2013.01)

(58) Field of Classification Search

CPC ....... A61B 5/0816; A61B 5/0873; G06T 5/50; G06T 5/70; G06T 7/194; G06T 2207/20224; G06V 40/103

See application file for complete search history.

(56) References Cited

U.S. PATENT DOCUMENTS

| | | | | |
|---|---|---|---|---|
| 6,352,517 | B1 | 3/2002 | Flock et al. | |
| 6,893,404 | B2 | 5/2005 | Ragnarsdottir | |
| 7,403,638 | B2 | 7/2008 | Jeung et al. | |
| 9,301,710 | B2 | 4/2016 | Mestha et al. | |
| 9,788,762 | B2 | 10/2017 | Auerbach | |
| 9,999,355 | B2 | 6/2018 | Kirenko | |
| 10,045,737 | B2 | 8/2018 | Tzvieli et al. | |
| 11,617,520 | B2 | 4/2023 | Addison et al. | |
| 2005/0201509 | A1 | 9/2005 | Mostafavi et al. | |
| 2011/0144517 | A1 | 6/2011 | Cervantes | |
| 2013/0345589 | A1* | 12/2013 | Laura Lapoint | A61B 5/0803 600/529 |

(Continued)

FOREIGN PATENT DOCUMENTS

CN 202311488529 A * 1/2024 ............. G06V 10/62

*Primary Examiner* — Tom Y Lu

(74) *Attorney, Agent, or Firm* — Alston & Bird LLP

(57) ABSTRACT

Various embodiments provide systems, devices and methods for determining breath rate by capturing a plurality of image frames from a region of interest, determining a subset of image frames that include image frames having largest movement values in the plurality of image frames, determining a first image frame in the subset of image frames and a last image frame in the subset of image frames. In various embodiments, the systems, devices and methods determine the breath rate using the first image frame and the last image frame in the subset of image frames and a rate of capturing the plurality of image frames.

20 Claims, 9 Drawing Sheets

(56) References Cited

U.S. PATENT DOCUMENTS

| | | | | |
|---|---|---|---|---|
| 2014/0236036 | A1* | 8/2014 | de Haan | A61B 5/725 600/534 |
| 2015/0073281 | A1 | 3/2015 | Mestha et al. | |
| 2019/0000375 | A1* | 1/2019 | Ferreira Dos Santos Da Fonseca | A61B 5/11 |
| 2020/0093425 | A1* | 3/2020 | Bhattacharjee | G06V 20/695 |
| 2022/0211333 | A1 | 7/2022 | Jacquel et al. | |
| 2024/0293078 | A1* | 9/2024 | Carter | A61B 5/7267 |

* cited by examiner

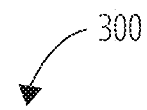

CAPTURE A PLURALITY OF IMAGE FRAMES FROM A REGION OF INTEREST 302

DETERMINE A MOVEMENT VALUE FOR EACH IMAGE FRAME OF THE PLURALITY OF IMAGE FRAMES 304

SELECT A SUBSET OF IMAGE FRAMES WHERE THE MOVEMENT VALUE CORRESPONDING TO EACH OF THE IMAGE FRAMES IN THE SUBSET OF IMAGE FRAMES IS MORE THAN THE MOVEMENT VALUE CORRESPONDING TO ANY OTHER FRAME IN THE PLURALITY OF THE IMAGE FRAMES 306

DETERMINE THE BREATH RATE USING THE SUBSET OF IMAGE FRAMES AND A RATE OF CAPTURING THE PLURALITY OF IMAGE FRAMES 308

FIG. 3

DETERMINE TWO DIMENSIONAL COORDINATES OF EACH PIXEL IN THE REGION OF INTEREST FOR THE IMAGE FRAME 402

DETERMINE A MOVEMENT VECTOR CORRESPONDING TO THE PIXEL IN THE REGION OF INTEREST BETWEEN ANY TWO CONSEQUENT IMAGE FRAMES USING A DIFFERENCE BETWEEN THE TWO DIMENSIONAL COORDINATES OF THE PIXEL IN THE TWO CONSEQUENT IMAGE FRAMES 404

DETERMINE A MOVEMENT VALUE FOR THE PIXEL OF THE IMAGE FRAME BY CALCULATING AN ABSOLUTE VALUE OF THE MOVEMENT VECTOR CORRESPONDING TO THE PIXEL 406

DETERMINE THE MOVEMENT VALUE FOR THE IMAGE FRAME BY CALCULATING A SUM OF MOVEMENT VALUES OF ALL PIXELS IN THE IMAGE FRAME 408

FIG. 4

DETERMINE, BY THE COMPUTING DEVICE, THE MOVEMENT VALUE FOR ALL IMAGE FRAMES IN THE PLURALITY OF IMAGE FRAMES 602

DETERMINE, BY THE COMPUTING DEVICE, A MAXIMUM DEVIATION IN THE MOVEMENT VALUE FOR ALL IMAGE FRAMES IN THE PLURALITY OF IMAGE FRAMES 604

COMPARE, BY THE COMPUTING DEVICE, THE MAXIMUM DEVIATION IN THE MOVEMENT VALUE WITH A DEVIATION MOVEMENT THRESHOLD 606

INCREASE, BY THE COMPUTING DEVICE, THE DEVIATION MOVEMENT THRESHOLD WHEN AN AMBIENT LIGHT INTENSITY IS LOWER THAN AN AMBIENT LIGHT THRESHOLD 608

DETERMINE, BY THE COMPUTING DEVICE, THAT HUMAN BREATHING IS NOT DETECTED WHEN THE MAXIMUM DEVIATION IN THE MOVEMENT VALUE IS LESS THAN THE DEVIATION MOVEMENT THRESHOLD 610

FIG. 6

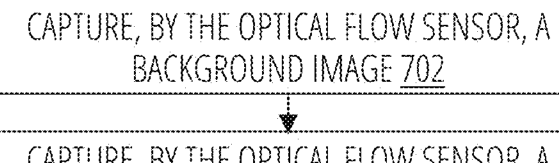
CAPTURE, BY THE OPTICAL FLOW SENSOR, A FOREGROUND IMAGE 704
DETERMINE, BY THE COMPUTING DEVICE, A SUBTRACTION IMAGE 706
REMOVE, BY THE COMPUTING DEVICE, NOISE FROM THE SUBTRACTION IMAGE 708
RECOGNIZE, BY THE COMPUTING DEVICE, A HUMAN IMAGE 710
DETERMINE, BY THE COMPUTING DEVICE, THE REGION OF INTEREST AS A REGION SURROUNDING THE HUMAN IMAGE 712
FIG. 7

CAPTURE A PLURALITY OF IMAGE FRAMES FROM A REGION OF INTEREST 802

DETERMINE A SUBSET OF IMAGE FRAMES THAT INCLUDE IMAGE FRAMES HAVING LARGEST MOVEMENT VALUES IN THE PLURALITY OF IMAGE FRAMES 804

DETERMINE A FIRST IMAGE FRAME IN THE SUBSET OF IMAGE FRAMES AND A LAST IMAGE FRAME IN THE SUBSET OF IMAGE FRAMES 806

DETERMINE THE BREATH RATE USING THE FIRST IMAGE FRAME AND THE LAST IMAGE FRAME IN THE SUBSET OF IMAGE FRAMES AND A RATE OF CAPTURING THE PLURALITY OF IMAGE FRAMES 808

FIG. 8

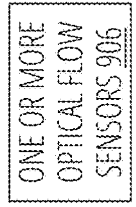
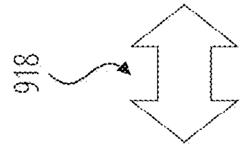
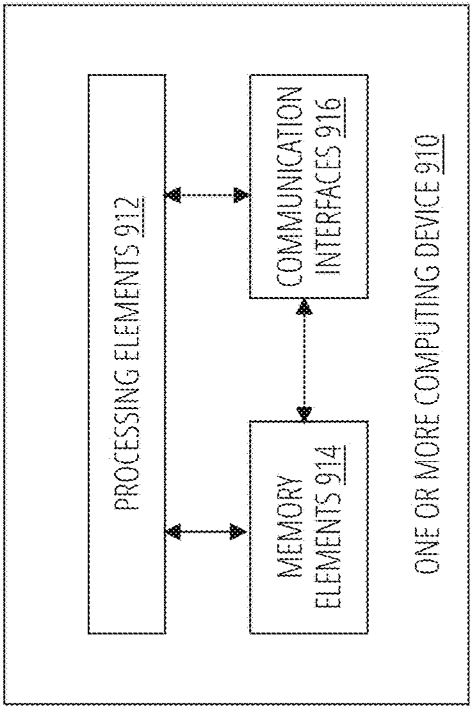
FIG. 9

SYSTEMS, DEVICES, AND METHODS FOR DETERMINING BREATH RATE USING AN OPTICAL FLOW SENSING

TECHNICAL FIELD

Embodiments of the present disclosure are generally directed to systems, devices, and methods for determining breath rate. In particular, some embodiments of the present disclosure relate to systems, devices, and methods for determining breath rate using optical flow sensing.

BACKGROUND

Breath rate detection apparatuses may be used to determine a rate of breathing or respiration. Some breath rate detection systems, methods, or apparatuses use cameras to determine breath rate. However, they may suffer from high processing or memory requirements. Through applied effort, ingenuity, and innovation, many of these identified problems have been solved by developing solutions that are included in embodiments of the present disclosure, examples of which are described in detail herein.

BRIEF SUMMARY

Various embodiments of the present disclosure provide breath rate detection method. The method may comprise capturing, by an optical flow sensor, a plurality of image frames from a region of interest; determining, by a computing device, a movement value for each image frame of the plurality of image frames; selecting, by a computing device, a subset of image frames where the movement value corresponding to each of the image frames in the subset of image frames is more than the movement value corresponding to any other frame in the plurality of the image frames; and determining, by the computing device, the breath rate using the subset of image frames and a rate of capturing the plurality of image frames.

In various embodiments, the breath rate detection method further comprises determining, by the computing device, a count for each image frame of the plurality of image frames; determining, by the computing device, a lowest count in the subset of image frames; and determining, by the computing device, a highest count in the subset of image frames.

In various embodiments, the breath rate detection method further comprises determining, by the computing device, a breathing frame count by subtracting the lowest count in the subset of image frames from the highest count in the subset of image frames.

In various embodiments, the breath rate detection method further comprises determining, by the computing device, a breath duration by dividing the breathing frame count with the rate of capturing the plurality of image frames.

In various embodiments, the breath rate detection method further comprises determining, by the computing device, the breath rate using the breath duration. In various embodiments, the breath rate detection method further comprises determining, by the computing device, a cardinality of the subset of image frames using the rate of capturing the plurality of image frames.

In various embodiments, the breath rate detection method further comprises determining, by the computing device, two dimensional coordinates of each pixel in the region of interest for the image frame, determining, by the computing device, a movement vector corresponding to the pixel in the region of interest between any two consequent image frames using a difference between the two dimensional coordinates of the pixel in the two consequent image frames, determining, by the computing device, a movement value for the pixel of the image frame by calculating an absolute value of the movement vector corresponding to the pixel, and determining, by the computing device, the movement value for the image frame by calculating a sum of movement values of all pixels in the image frame.

In various embodiments, the breath rate detection method further comprises determining, by the computing device, the movement value for all image frames in the plurality of image frames, determining, by the computing device, a maximum deviation in the movement value for all image frames in the plurality of image frames, comparing, by the computing device, the maximum deviation in the movement value with a deviation movement threshold, increasing, by the computing device, the deviation movement threshold when an ambient light intensity is lower than an ambient light threshold, and determining, by the computing device, that human breathing is not detected when the maximum deviation in the movement value is less than the deviation movement threshold.

In various embodiments, the breath rate detection method further comprises capturing, by the optical flow sensor, a background image, capturing, by the optical flow sensor, a foreground image, determining, by the computing device, a subtraction image by subtracting a multiplication of the background image with the foreground image from the foreground image, removing, by the computing device, noise from the subtraction image, recognizing, by the computing device, a human image, and determining, by the computing device, the region of interest as a region surrounding the human image.

Various embodiments provide an apparatus for detecting breath rate, the apparatus comprising at least one processor and at least one non-transitory memory including computer coded instructions thereon, the computer coded instructions, with the at least one processor, cause the apparatus to capture a plurality of image frames from a region of interest, determine a movement value for each image frame of the plurality of image frames, select a subset of image frames where the movement value corresponding to each of the image frames in the subset of image frames is more than the movement value corresponding to any other frame in the plurality of the image frames, and determine the breath rate using the subset of image frames and a rate of capturing the plurality of image frames.

In various embodiments, the computer coded instructions further cause the apparatus to determine a count for each image frame of the plurality of image frames, determine a lowest count in the subset of image frames, and determine a highest count in the subset of image frames.

In various embodiments, the computer coded instructions further cause the apparatus to determine a breathing frame count by subtracting the lowest count in the subset of image frames from the highest count in the subset of image frames.

In various embodiments, the computer coded instructions further cause the apparatus to determine a breath duration by dividing the breathing frame count with the rate of capturing the plurality of image frames.

In various embodiments, the computer coded instructions further cause the apparatus to determine the breath rate using the breath duration.

In various embodiments, the computer coded instructions further cause the apparatus to determine a cardinality of the subset of image frames using the rate of capturing the plurality of image frames.

In various embodiments, the computer coded instructions further cause the apparatus to determine two dimensional coordinates of each pixel in the region of interest for the image frame, determine a movement vector corresponding to the pixel in the region of interest between any two consequent image frames using a difference between the two dimensional coordinates of the pixel in the two consequent image frames, determine a movement value for the pixel of the image frame by calculating an absolute value of the movement vector corresponding to the pixel, and determine the movement value for the image frame by calculating a sum of movement values of all pixels in the image frame.

In various embodiments, the computer coded instructions further cause the apparatus to determine the movement value for all image frames in the plurality of image frames, determine a maximum deviation in the movement value for all image frames in the plurality of image frames, compare the maximum deviation in the movement value with a deviation movement threshold, increase the deviation movement threshold when an ambient light intensity is lower than an ambient light threshold, and determine that human breathing is not detected when the maximum deviation in the movement value is less than the deviation movement threshold.

In various embodiments, the computer coded instructions further cause the apparatus to capture a background image, capture a foreground image, determine a subtraction image using the background image and the foreground image, remove noise from the subtraction image, recognize a human image, and determine the region of interest as a region surrounding the human image.

Various embodiments provide a breath rate detection method comprising capturing, by an optical flow sensor, a plurality of image frames from a region of interest, determining, by a computing device, a subset of image frames that include image frames having largest movement values in the plurality of image frames, determine a first image frame in the subset of image frames and a last image frame in the subset of image frames, and determining, by the computing device, the breath rate using the first image frame and the last image frame in the subset of image frames and a rate of capturing the plurality of image frames.

In various embodiments, the breath rate detection method further comprising determining, by the computing device, two dimensional coordinates of each pixel in the region of interest for each image frame in the plurality of image frames, determining, by the computing device, a movement vector corresponding to the pixel in the region of interest between any two consequent image frames using a difference between the two-dimensional coordinates of the pixel in the two consequent image frames, determining, by the computing device, a movement value for the pixel of the image frame by calculating an absolute value of the movement vector corresponding to the pixel, and determining, by the computing device, a movement value for the image frame by calculating a sum of movement values of all pixels in the image frame.

BRIEF DESCRIPTION OF THE SEVERAL VIEWS OF THE DRAWINGS

FIG. 3 illustrates a method 300 in accordance with various embodiments.

FIG. 4 illustrates a method 400 in accordance with various embodiments.

FIG. 6 illustrates a method 600 in accordance with various embodiments.

FIG. 7 illustrates a method 700 in accordance with various embodiments.

FIG. 8 illustrates a method 800 in accordance with various embodiments.

FIG. 9 illustrates a breath rate detection apparatus 900 in accordance with various embodiments.

DETAILED DESCRIPTION

Figure 1:
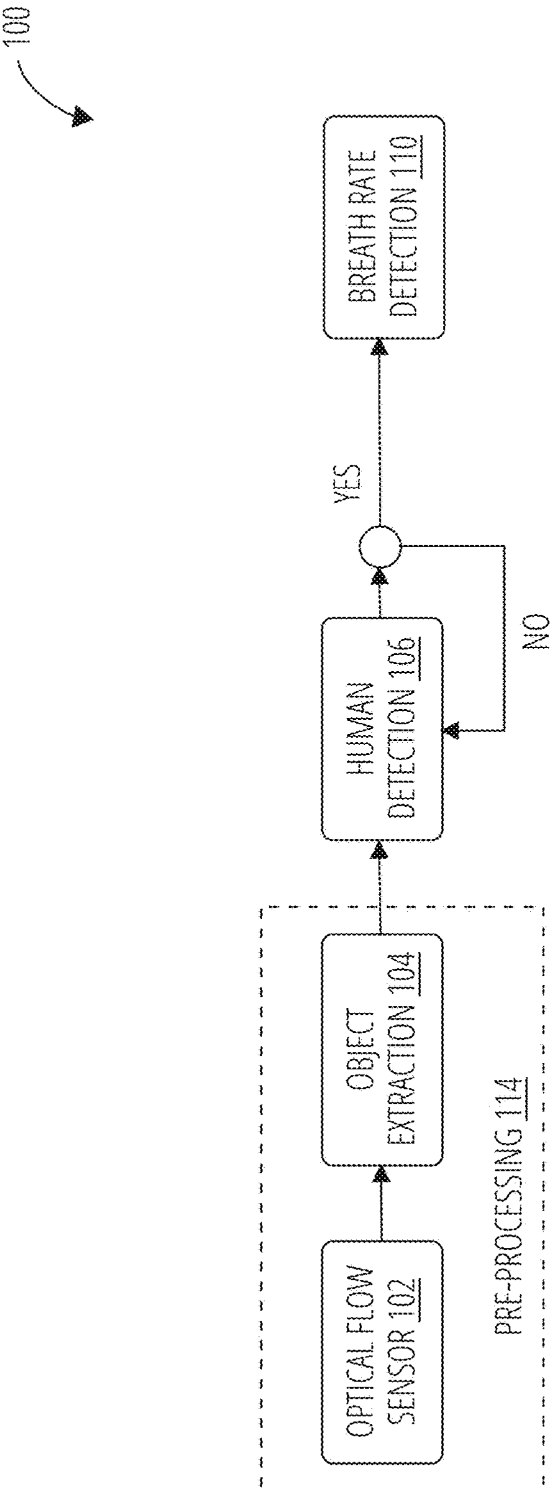
FIG. 1 illustrates various aspects of a breath rate detection system 100 in accordance with various embodiments.

The phrases "in one embodiment," "according to one embodiment," "in some embodiments," "in various embodiments" and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration" without a limitation. Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such a component or feature may be optionally included in some embodiments, or it may be excluded.

Use of broader terms such as "comprises," "includes," and "having" should be understood to provide support for narrower terms such as "consisting of," "consisting essentially of," and "comprised substantially of". Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

The term "computing device" refers to any computer, controller (such as a microcontroller), processor, circuitry, and/or other executor of computer instructions that is embodied in hardware, software, firmware, and/or any combination thereof, that enables access to myriad functionalities associated with one or more mobile device(s), system(s), and/or one or more communications networks. Non-limiting examples of a computing device include a computer, a controller (such as a microcontroller), an application-specific integrated circuit, a field-programmable gate array, a personal computer, a smart phone, a laptop, a fixed terminal, a server, a networking device, a virtual machine, a processor, a plurality of processors electronically coupled to each other and placed in proximity of each other, remote from each other, in a various groups or bundles of one or more processors, and/or forming cloud computing or processing, etc. Other examples of computing devices are provided herein.

The term "electronically coupled," "electronically coupling," "electronically couple," "in electronic communication with," or "electronically connected" in the present disclosure refers to two or more elements or components being electronically connected, directly or indirectly. For example, two or more elements or components may be connected through wired means and/or wireless means, such that signals, voltage/current, data, information, or any other electronic signals may be transmitted to and/or received from these elements or components. Electronic connections established via an electrical connector and/or port may refer to wired connections.

It is important to detect human breathing rate for vital sensing, safety monitoring, etc. For example, it may be desirable to monitor breathing and/or detect breath rate of babies, children of various ages, seniors, patients, etc., to ensure their safety.

It may also be desirable to determine breath rate without physical contact to the body. Not requiring a physical contact with the body may make the systems and devices easier to use, less intrusive, provide flexibility of movement for the subject, provide monitoring without or with less interruptions, etc.

However, it may be challenging to estimate breath rate without any contact to the body. For example, capturing images of the subject using conventional cameras, such as RGB cameras, may be memory consuming and privacy may not be protected sufficiently. In some examples, due to large file sizes, large memory spaces may be needed for storage and/or image processing using cameras. Also, cameras may capture images of human face and/or body, hence encroaching on the privacy of the subject.

Various embodiments of the present disclosure use an optical flow sensor to sense optical flow, and provide signal processing including AI algorithms to human breath rate. In various embodiments, an optical flow sensor may sense and capture movement, including movement of objects, in the field of view.

In various embodiments, moving vectors are obtained by the optical flow sensor and are used to detect human and respiratory rate. Various embodiments may for example provide contactless breath rate recognition and privacy protection, while causing small memory footprint. Therefore, example embodiments may require computing devices without a need for a large memory to run the provided algorithms. Various examples may for example measure the breath rate using a low frame per second optical flow sensor, further reducing memory footprint, processing requirements, power consumption, and/or cost, etc.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

The components illustrated in the figures represent components that may or may not be present in various embodiments of the present disclosure described herein such that embodiments may include fewer or more components than those shown in the figures while not departing from the scope of the present disclosure. Some components may be omitted from one or more figures or shown in dashed line for visibility of the underlying components.

Referring now to FIG. 1 a block diagram illustrating a breath rate detection system 100 is provided in accordance with various embodiments of the present disclosure.

In various embodiments, a pre-processing sub-system 114 includes an optical flow sensor 102. The optical flow sensor 102 may determine a difference between any two image frames captured by determining moving vectors associated with each pixel in the field of view in adjacent image frames.

For example, the optical flow sensor 102 determines (x,y,dx,dy) for each pixel in the field of view. (x,y) may denote the coordinates of the pixel in the field of view and (dx,dy) may denote a change in the coordinates between adjacent image frames.

In various embodiments, an object extraction module 104 uses the output generated by the optical flow sensor 102 to extract an object in the field of view. In various embodiments, using signal processing methods, a noise reduction step may also be performed in the pre-processing sub-system 114. For example, a noise reduction filter may be applied in the pre-processing sub-system 114. In various embodiments, pre-processing sub-system 114 generates a plurality of binarized image with various pixels having value 1 (or 0) when a movement is detected or value 0 (or 1) when a movement is not detected at the pixel location.

In various embodiments, the breath rate detection system 100 includes a human detection module 106. The human detection module 106 may apply a neural network model to an output of the pre-processing sub-system 114 to determine whether the detected object is a human or not. In example embodiments, the neural network model may include various deep learning models or convolutional neural network models. In various embodiments, the pre-processing sub-system 114 selects a region of interest surrounding the extracted object and the human detection module 106 applies the human detection model to the object in the region of interest.

In various embodiments, if a human is detected in the region of interest, a breath rate detection module 110 determines the breath rate using a plurality of image frames captured by the optical flow sensor 102.

Figure 2:
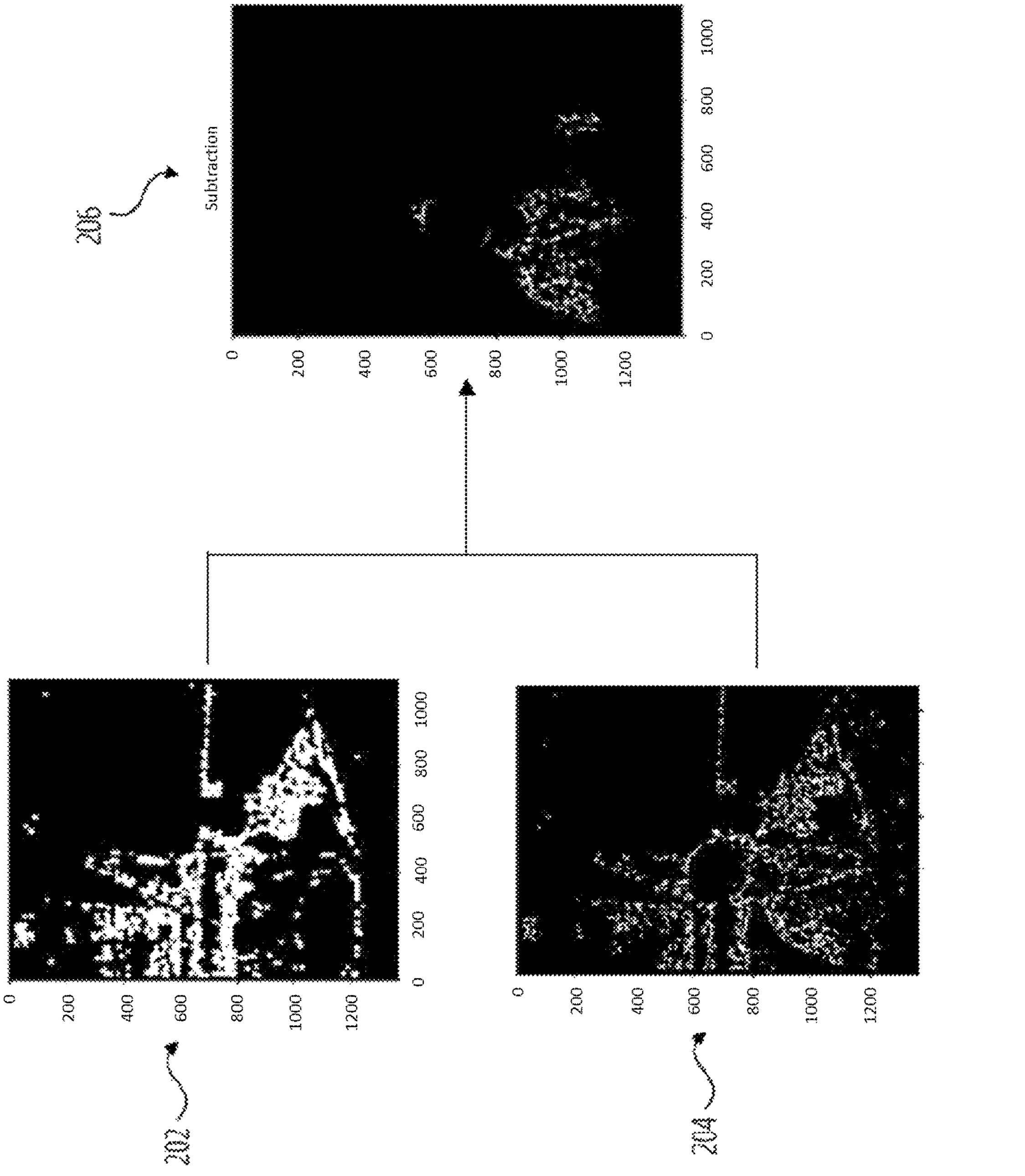
FIG. 2 illustrates a captured images in accordance with various embodiments.

Referring now to FIG. 2 a diagram illustrating determining a human in the region of interest is provided in accordance with various embodiments of the present disclosure.

In various embodiments, one or more image frames are accumulated to provide background noise cancellation. In various embodiments, one or more background image frames 202 are determined. In various embodiments, one or more foreground image frames 204 are determined. In various embodiments, background noise is determined using the one or more background image frames 202 and the subtraction image 206 is determined. In various embodiments, the foreground image frame is multiplied with the background image frame to generate an overlapped image frame. A subtraction image frame is generated by subtracting the overlapped image frame from the foreground image frame. Therefore, foreground and background image frames are used to generate a subtraction image frame. In various embodiments, the subtraction image includes less of the undesired background image details. In various embodiments, various outlier pixels where a movement is detected may be eliminated, since the outlier points are very likely created due to noise and not human breathing and/or movement.

Referring now to FIG. 3 a flowchart illustrating a method 300 is provided in accordance with various embodiments of the present disclosure.

In various embodiments, at step 302, method 300 captures a plurality of image frames from a region of interest. In various embodiments, the method 300 captures the plurality of image frames, by an optical flow sensor.

In various embodiments, at step 304, method 300 determines a movement value for each image frame of the plurality of image frames. In various embodiments, the method 300 determines the movement value by a computing device.

For example, method 300 determines two dimensional coordinates of each pixel in the region of interest for the image frame. For example, as previously described, coordinates (x,y) may be determined for each pixel in the region of interest. In various embodiments, the method 300 determines a movement vector corresponding to each pixel in the region of interest between any two consequent image frames. In various embodiments, the movement vector is determined using a difference between the two-dimensional coordinates of the pixel in the two consequent image frames. For example, the movement vector is determined using a difference between the two-dimensional coordinates of the pixel in two consequent image frames. In various embodiments, the movement vector is determined for any two consequent pair of image frames.

In various embodiments, the movement value is determined using the movement vector. For example, the movement value is determined by calculating an absolute value, such as by using root mean square value, of the movement vector corresponding to the pixel.

In various embodiments, the method 300 determines the movement value for an image frame by calculating a sum of the movement values of all the pixels in the image frame. In various embodiments, a movement value is determined for each image frame of the plurality of image frames.

In various embodiments, the movement vector corresponding to each pixel at each image frame is determined with respect to the previous image frame. Therefore, in various embodiments, the movement vector denoted a movement of a pixel in an image frame with respect to a previous image frame in the plurality of image frames. Therefore, in various embodiments, the movement value for an image frame denotes a total movement of the pixels in the image frame with respect to a prior image frame in the plurality of image frames.

In various embodiments, at step 306, method 300 selects a subset of image frames. In various embodiments, the method 300 selects a subset of image frames by a computing device. The subset of image frames may be selected such that the movement value corresponding to each of the image frames in the subset of image frames is more than the movement value corresponding to any other frame in the plurality of the image frames.

Therefore, in accordance with various embodiments, the movement values corresponding to the image frames in the subset of image frames are the highest movement values of the image frames in the plurality of image frames. In example embodiments, when there is a high increase of movement value among adjacent image frames, it may indicate a start of a breathing period (breathing in or breathing out). In example embodiments, when the movement value among adjacent frames doesn't vary much, it may indicate a half cycle in a breathing period (e.g., breathing in or breathing out has ended). In example embodiments, when once again there is a high increase of movement value among adjacent image frames, it may indicate that a breathing period has started again (breathing out or breathing in). In example embodiments, when the movement value among adjacent frames doesn't vary much again, it may indicate the end of the breathing period.

In various embodiments, the computing device may select a known number of the image frames that have the highest movement values among all the image frames, as the subset of image frames. The known number may be determined using a frame rate of the optical flow sensor. In various embodiments, the frame rate of the optical flow sensor may determine the rate of capturing the plurality of image frames. Therefore, the cardinality of the subset of image frames may be determined using the rate of capturing the plurality of image frames.

In various embodiments, the movement value for each image frame in the subset of image frames is a local peak of movement values among its adjacent image frames. Therefore, in various embodiments, a known number of local peaks of movement values is selected and the corresponding image frames are included in the subset of image frames.

In various embodiments, the total number of the plurality of image frames captured is determined using the rate of capturing the plurality of image frames and average human breathing time period. For example, the total number of the plurality of image frames is selected such that the duration of capturing the plurality of image frames using the rate of capturing the plurality of image frames spans at least one full duration of human breathing period.

In various embodiments, when a higher rate of capturing the plurality of image frames is used, a higher number of image frames are selected in the subset of image frames. In various embodiments, when a lower rate of capturing the plurality of image frames is used, a lower number of image frames are selected in the subset of image frames.

In an example, 40 image frames may be captured at a rate of capturing the plurality of image frames of 6 frames per second. In this example, at about 6.6 seconds the breath rate may be determined. In this example, the cardinality of the subset of image frames may be 5 image frames. It is noted that these values are for example purposes only, and in various embodiments, other values may be used, for example values in proximity of this presented example. For example, 30-50 image frames may be captured using 4-8 frames per second rate of capturing the plurality of image frames and the cardinality of the subset of image frames may be selected to be in the range of 4-8 image frames.

In various embodiments, at step 308, method 300 determines the breath rate using the subset of image frames and a rate of capturing the plurality of image frames. The method 300 may use a computing device to determine the breath rate using the subset of image frames and a rate of capturing the plurality of image frames. Determining the breath rate using the subset of image frames and the rate of capturing the plurality of image frames is described further with reference to FIG. 5, in accordance with various embodiments of the present disclosure.

Referring now to FIG. 4 a flowchart illustrating a method 400 is provided in accordance with various embodiments of the present disclosure.

In various embodiments, the method 400 is used to determine the movement value corresponding to an image frame, as for example used in method 300. In various embodiments, at step 402, method 400 determines, e.g., by the computing device, two dimensional coordinates of each pixel in the region of interest for the image frame. In various embodiments, at step 404, method 400 determines, e.g., by the computing device, a movement vector corresponding to the pixel in the region of interest between any two consequent image frames using a difference between the two-dimensional coordinates of the pixel in the two consequent image frames. In various embodiments, at step 406, method 400 determines, e.g., by the computing device, a movement value for the pixel of the image frame by calculating an absolute value of the movement vector corresponding to the pixel. In various embodiments, at step 408, method 400 determines, e.g., by the computing device, the movement value for the image frame by calculating a sum of movement values of all pixels in the image frame.

Figure 5:
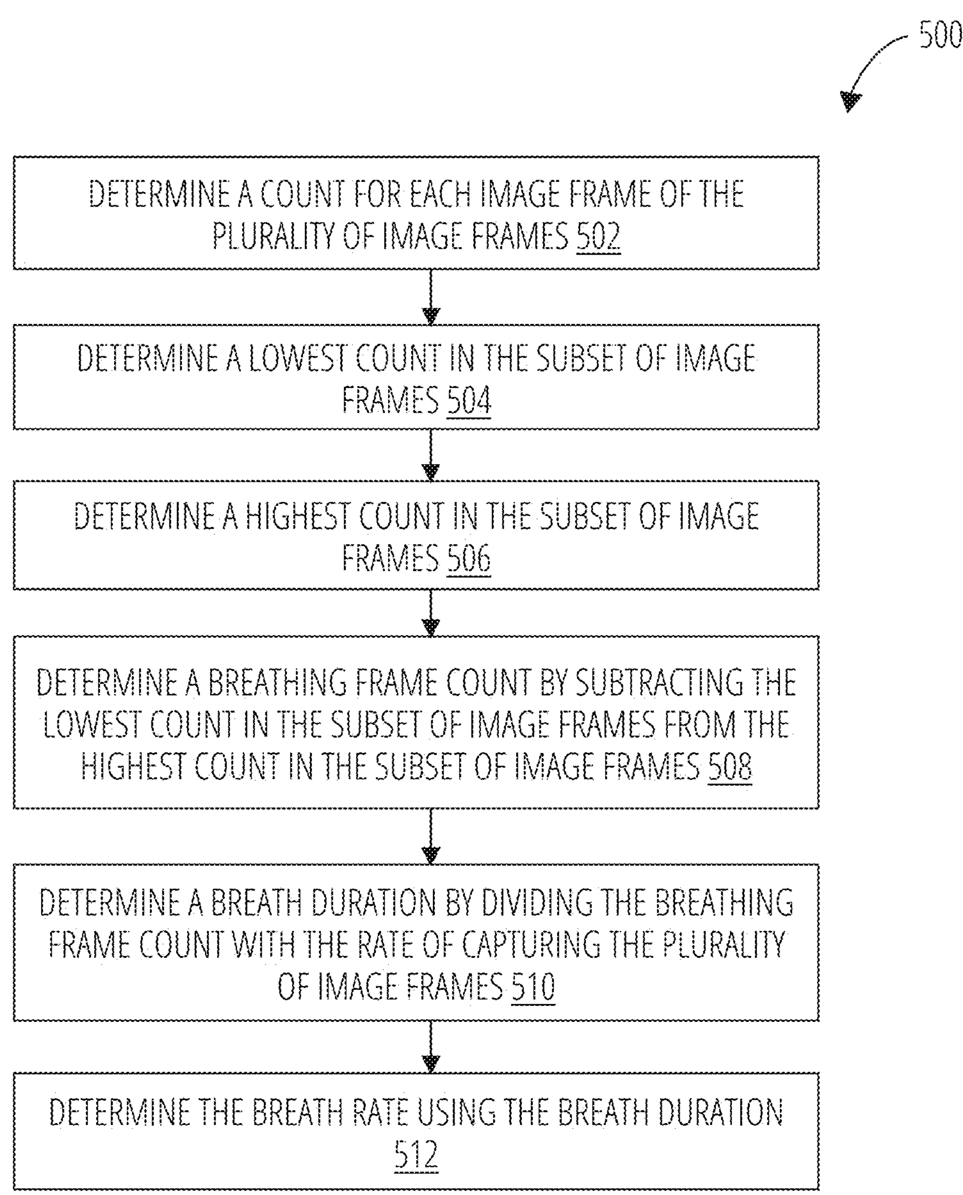
FIG. 5 illustrates a method 500 in accordance with various embodiments.

Referring now to FIG. 5 a schematic diagram illustrating a method 500 is provided in accordance with various embodiments of the present disclosure.

In various embodiments, the method includes determining a count for each image frame of the plurality of image frames at step 502. For example, the count for each image frame may be an integer number assigned to each image frame starting from 1 for the first image frame captured, and N for the $N^{th}$ image frame captured, where N is an integer.

In various embodiments, the method includes determining a lowest count in the subset of image frames at step 504. For example, the count of (e.g., assigned integer value to) an image frame in the subset of image frames (as e.g., selected at step 306 by method 300) with the lowest value is determined.

In various embodiments, the method includes determining a highest count in the subset of image frames at step 506. For example, the count of (e.g., assigned integer value to) an image frame in the subset of image frames (as e.g., selected at step 306 by method 300) with the highest value is determined.

In various embodiments, the method includes determining a breathing frame count by subtracting the lowest count in the subset of image frames from the highest count in the subset of image frames at step 508. In various embodiments, the breathing frame count may indicate the number of image frames in which a full breathing period takes place.

For example, among 40 image frames captured by an optical flow sensor from the region of interest, image frame numbers 8,12,23,27,32 may have the highest values (or are the local peaks) of movement values among all image frames. In this example, the highest count in the subset of image frames is 32 and the lowest count in the subset of image frames is 8. Subtracting the lowest count in the subset of image frames from the highest count in the subset of image frames would be 32−8=24. Therefore, in this example, the breathing frame count is 24.

According to some examples, the method includes determining a breath duration by dividing the breathing frame count with the rate of capturing the plurality of image frames at step 510. In the example above, if the rate of capturing the plurality of image frames is 6 frames per second, the breath duration is determined to be 24/6 or 4 seconds. In this example, the breath duration, or the time of one breath period is determined to be 4 seconds.

According to some examples, the method includes determining the breath rate using the breath duration at step 512. For example, the breath rate may be determined as breath/minute, in such case the breath rate is determined by dividing 60 by the breath duration.

Referring now to FIG. 6 a schematic diagram illustrating method 600 is provided in accordance with various embodiments of the present disclosure.

In various embodiments, at step 602, method 600 determines, e.g., by the computing device, the movement value for all the image frames in the plurality of image frames.

In various embodiments, at step 604, method 600 determines, e.g., by the computing device, a maximum deviation in the movement value for all image frames in the plurality of image frames. For example, the maximum deviation in the movement value denotes the maximum amount of variation in the movement values of the image frames in the plurality of image frames.

In various embodiments, at step 606, method 600 compares, e.g., by the computing device, the maximum deviation in the movement value with a deviation movement threshold. For example, by doing so, the method 600 may determine whether the movement values of the image frames in the plurality of captured image frames vary much or not.

In various embodiments, at step 608, method 600 increases, by the computing device, the deviation movement threshold when an ambient light intensity is lower than an ambient light threshold. In various examples, in dark conditions, more noise may be generated. By increasing the deviation movement threshold when the ambient light intensity is lower than the ambient light threshold, the method 600 accounts for larger noise that may be present in darker conditions.

In various embodiments, at step 610, method 600 determines, by the computing device, that human breathing is not detected when the maximum deviation in the movement value is less than the deviation movement threshold. For example, method 600 determines that a detected human is not breathing or has stopped breathing. In various embodiments, by determining that the movement values of the image frames in the plurality of captured image frames do not vary much, the method 600 determines that a detected human is not breathing or has stopped breathing.

Referring now to FIG. 7 a schematic diagram illustrating a method 700 is provided in accordance with various embodiments of the present disclosure.

In various embodiments, at step 702, method 700 captures a background image. For example, the method 700 captures the background image by the optical flow sensor 102. In various embodiments, the background image is determined using a plurality of captured background image frames. In various embodiments, at step 704, method 700 captures a foreground image. In various embodiments, the foreground image is determined using a plurality of captured foreground image frames. For example, the method 700 captures the foreground image by the optical flow sensor 102.

In various embodiments, at step 706, method 700 determines, e.g., by the computing device, a subtraction image. In various embodiments, the foreground image and background image are used for generating subtraction image. For example, the method 700 multiplies the background image with the foreground image to generate an overlapped image. In various embodiments, the method 700 subtracts the overlapped image from the foreground image to generate the subtraction image. For example, subtraction image=(foreground image−(foreground image*background image)).

In various embodiments, at step 708, method 700 removes, e.g., by the computing device, noise from the subtraction image. For example, the method 700 may remove any outlier remaining data points in an image as noise.

In various embodiments, at step 710, method 700 recognizes, e.g., by the computing device, a human image. For example, the method 700 may use various Artificial Intelligence (AI) algorithms, machine learning (ML) algorithms, neural network such as convolutional neural networks, deep learning techniques, etc., to recognize a human image. In various embodiments, breath rate detection may occur after a human is recognized. In various embodiments, breath rate detection may occur regardless of, or without a human recognition, or before a human is recognized.

In various embodiments, at step 712, method 700 determines, e.g., by the computing device, the region of interest as a region surrounding the human image.

In various embodiments, a region of interest may be determined in various other ways, for example without a human recognition. In various embodiments, the region of interest may be any part, up to the entire field of view.

Referring now to FIG. 8 a schematic diagram illustrating a method 800 is provided in accordance with various embodiments of the present disclosure.

In various embodiments, at step 802, method 800 captures, by an optical flow sensor, a plurality of image frames from a region of interest. In various embodiments, the region of interest may be any part, up to the entire field of view. In various embodiments, a human may be present in the region of interest.

In various embodiments, at step 804, method 800 determines, e.g., by a computing device, a subset of image frames that include image frames having largest movement values in the plurality of image frames. Therefore, in various embodiments, the image frames in the subset of image frames have corresponding movement values larger than movement values of any other image frame that is not in the subset of image frames.

In various embodiments, at step 806, method 800 determines a first image frame in the subset of image frames and a last image frame in the subset of image frames. In various embodiments, the image frames in the subset of image frames are sequenced with the same sequence of capturing of the image frames. Therefore, the first image frame in the subset of image frames may be captured the earliest and the last image frame in the subset of image frames may be captured the latest in the subset of image frames.

In various embodiments, at step 808, method 800 determines, e.g., by the computing device, the breath rate using the first image frame and the last image frame in the subset of image frames and a rate of capturing the plurality of image frames. In various embodiments, first image frame in the subset of image frames has the lowest count in the subset of image frames and the last image frame in the subset of image frames has the highest count in the subset of image frames. In various embodiments, the breath rate is determined using the lowest count in the subset of image frames and the highest count in the subset of image frames as previously described.

Referring now to FIG. 9 a schematic diagram illustrating breath rate detection apparatus 900 is provided in accordance with various embodiments of the present disclosure. In various embodiments, the breath rate detection apparatus 900 includes one or more optical flow sensors 906.

In various embodiments, the breath rate detection apparatus 900 includes one or more computing device 910. In various embodiments, some or all of the one or more computing device 910 may be placed locally or in proximity with one or more optical flow sensors 906 (for example within a same housing) or remotely from one or more optical flow sensors 906 (for example outside the housing). In various embodiments, the one or more computing device 910 may be placed inside another housing.

In various embodiments, the one or more computing device 910 is in communication with various other components of the breath rate detection apparatus 900 through communication interfaces 916 and over the wired and/or wireless medium 918.

In general, the terms computing apparatus, computer, system, device, entity, and/or similar words used herein interchangeably can refer to, for example, one or more computers, computing entities, desktops, mobile phones, tablets, notebooks, laptops, distributed systems, kiosks, input terminals, servers or server networks, blades, gateways, switches, processing devices, processing entities, controllers, control systems, set-top boxes, relays, routers, network access points, base stations, the like, and/or any combination of devices or entities adapted to perform the functions, operations, and/or processes described herein. Such functions, operations, and/or processes can include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably. The one or more computing device 910 can include any computing device including, for example, a mobile device handling and/or processing apparatus configured to perform one or more steps/operations of one or more method or techniques described herein. In some embodiments, the one or more computing device 910 can include and/or be in association with one or more programmable logic controller (PLC), desktop computer(s), laptop(s), server(s), cloud computing platform(s), controller systems, and/or the like. In some example embodiments, the one or more computing device 910 can be configured to receive and/or transmit image processing instructions, data, and/or the like between the one or more breath rate detection apparatus 900 and/or their components to perform one or more steps/operations of one or more breath rate detection apparatus 900 handling and/or processing techniques described herein.

The one or more computing device 910 can include, or be in communications with, one or more processing elements 912 (also referred to as processors, processing circuitry, digital circuitry, and/or similar terms used herein interchangeably) that communicate with other elements within the one or more computing device 910 via a bus, for example. As will be understood, the processing elements 912 can be embodied in a number of different ways.

For example, the processing elements 912 can be embodied as one or more complex programmable logic devices (CPLDs), microprocessors, multi-core processors, coprocessing entities, application-specific instruction-set processors (ASIPs), microcontrollers, and/or controllers. Further, the processing elements 912 can be embodied as one or more other processing devices or circuitry. The term circuitry can refer to an entirely hardware embodiment or a combination of hardware and computer program products. Thus, the processing elements 912 can be embodied as integrated circuits, application specific integrated circuits (ASICs), field programmable gate arrays (FPGAs), programmable logic arrays (PLAs), hardware accelerators, digital circuitry, and/or the like.

As will therefore be understood, the processing elements 912 can be configured for a particular use or configured to execute instructions stored in volatile or non-volatile media or otherwise accessible to the processing elements 912. As such, whether configured by hardware or computer program products, or by a combination thereof, the processing elements 912 can be capable of performing steps or operations according to embodiments of the present disclosure when configured accordingly.

In one embodiment, the one or more computing device 910 can further include, or be in communication with, one or more memory elements 914. The one or more memory elements 914 can include non-volatile and/or volatile media. The memory elements 914, for example, can include non-volatile media (also referred to as non-volatile storage, memory, memory storage, memory circuitry and/or similar terms used herein interchangeably). In one embodiment, the non-volatile storage or memory can include one or more non-volatile storage or memory media, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media can store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably can refer to a collection of records or data that is stored in a computer-readable storage medium using one or more database models, such as a hierarchical database model, network model, relational model, entity—relationship model, object model, document model, semantic model, graph model, and/or the like.

In addition, or alternatively, the memory elements 914 can include volatile memory. For example, the one or more computing device 910 can further include, or be in communication with, volatile media (also referred to as volatile storage memory, memory storage, memory circuitry and/or similar terms used herein interchangeably). In one embodiment, the volatile storage or memory can also include one or more volatile storage or memory media, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media can be used to store at least portions of the databases, database instances, database management systems, data, applications, programs, program modules, scripts, source code, object code, byte code, compiled code, interpreted code, machine code, executable instructions, and/or the like being executed by, for example, the processing elements 912. Thus, the databases, database instances, database management systems, data, applications, programs, program modules, scripts, source code, object code, byte code, compiled code, interpreted code, machine code, executable instructions, and/or the like can be used to control certain aspects of the operation of the one or more computing device 910 with the assistance of the processing elements 912 and operating system.

As indicated, in one embodiment, the one or more computing device 910 can also include one or more communication interfaces 916 for communicating with various computing entities, such as by communicating data, content, information, and/or similar terms used herein interchangeably that can be transmitted, received, operated on, processed, displayed, stored, and/or the like. Such communication can be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the one or more computing device 910 can be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

The fire detection system breath rate detection apparatus 900 can include input/output circuitry for communicating with one or more users or other systems or devices. The input/output circuitry, for example, can include one or more interfaces for providing and/or receiving information from one or more users or other systems or devices fire detection system breath rate detection apparatus 900 or otherwise such as providing alarms, alerts (for example when no breath rate is detected or breath rate below and/or above a breath rate threshold is detected), and/or breath rate information. The input/output circuitry can be configured to receive user input or input from various other systems or devices through one or more of the interfaces of the breath rate detection apparatus 900.

The one or more computing device 910 may perform various steps of various methods provided in accordance with various embodiments of the present disclosure.

Although the methods in accordance with various embodiments provided above depict a particular sequence of operations, the sequence may be altered without departing from the scope of the present disclosure. For example, some of the operations depicted may be performed in parallel or in a different sequence that does not materially affect the function of the methods in accordance with various embodiments. In other examples, different components of an example device or system that implements the methods in accordance with various embodiments may perform functions at substantially the same time or in a specific sequence.

What is claimed is:

1. A breath rate detection method comprising:

capturing, by an optical flow sensor, a plurality of image frames from a region of interest;

determining, by a computing device, a movement value for each image frame of the plurality of image frames;

selecting, by a computing device, a subset of image frames where the movement value corresponding to each of the plurality of image frames in the subset of image frames is more than the movement value corresponding to any other frame in the plurality of image frames; and determining, by the computing device, a breath rate using the subset of image frames and a rate of capturing the plurality of image frames.

2. The breath rate detection method of claim 1, further comprising:

determining, by the computing device, a count for each image frame of the plurality of image frames;

determining, by the computing device, a lowest count in the subset of image frames; and determining, by the computing device, a highest count in the subset of image frames.

3. The breath rate detection method of claim 2, further comprising determining, by the computing device, a breathing frame count by subtracting the lowest count in the subset of image frames from the highest count in the subset of image frames.

4. The breath rate detection method of claim 3, further comprising determining, by the computing device, a breath duration by dividing the breathing frame count with the rate of capturing the plurality of image frames.

5. The breath rate detection method of claim 4, further comprising determining, by the computing device, the breath rate using the breath duration.

6. The breath rate detection method of claim 1, further comprises determining, by the computing device, a cardinality of the subset of image frames using the rate of capturing the plurality of image frames.

7. The breath rate detection method of claim 1, further comprising:

determining, by the computing device, two dimensional coordinates of each pixel in the region of interest for each image frame in the plurality of image frames;

determining, by the computing device, a movement vector corresponding to each pixel in the region of interest between any two consequent image frames using a difference between the two dimensional coordinates of each pixel in the two consequent image frames;

determining, by the computing device, a movement value for each pixel of an image frame by calculating an absolute value of the movement vector corresponding to each pixel; and determining, by the computing device, the movement value for the image frame by calculating a sum of movement values of all pixels in the image frame.

8. The breath rate detection method of claim 1, further comprising:

determining, by the computing device, the movement value for all image frames in the plurality of image frames;

determining, by the computing device, a maximum deviation in the movement value for all image frames in the plurality of image frames;

comparing, by the computing device, the maximum deviation in the movement value with a deviation movement threshold;

increasing, by the computing device, the deviation movement threshold when an ambient light intensity is lower than an ambient light threshold; and determining, by the computing device, that human breathing is not detected when the maximum deviation in the movement value is less than the deviation movement threshold.

9. The breath rate detection method of claim 1, further comprising:

capturing, by the optical flow sensor, a background image;

capturing, by the optical flow sensor, a foreground image;

determining, by the computing device, a subtraction image by subtracting a multiplication of the background image with the foreground image from the foreground image;

removing, by the computing device, noise from the subtraction image;

recognizing, by the computing device, a human image; and determining, by the computing device, the region of interest as a region surrounding the human image.

10. An apparatus for detecting breath rate, the apparatus comprising at least one processor and at least one non-transitory memory including computer coded instructions thereon, the computer coded instructions, with the at least one processor, cause the apparatus to:

capture a plurality of image frames from a region of interest;

determine a movement value for each image frame of the plurality of image frames;

select a subset of image frames where the movement value corresponding to each of the image frames in the subset of image frames is more than the movement value corresponding to any other frame in the plurality of image frames; and determine the breath rate using the subset of image frames and a rate of capturing the plurality of image frames.

11. The apparatus of claim 10, wherein the computer coded instructions further cause the apparatus to:

determine a count for each image frame of the plurality of image frames;

determine a lowest count in the subset of image frames; and determine a highest count in the subset of image frames.

12. The apparatus of claim 11, wherein the computer coded instructions further cause the apparatus to determine a breathing frame count by subtracting the lowest count in the subset of image frames from the highest count in the subset of image frames.

13. The apparatus of claim 12, wherein the computer coded instructions further cause the apparatus to determine a breath duration by dividing the breathing frame count with the rate of capturing the plurality of image frames.

14. The apparatus of claim 13, wherein the computer coded instructions further cause the apparatus to determine the breath rate using the breath duration.

15. The apparatus of claim 10, wherein the computer coded instructions further cause the apparatus to determine a cardinality of the subset of image frames using the rate of capturing the plurality of image frames.

16. The apparatus of claim 10, wherein the computer coded instructions further cause the apparatus to:

determine two dimensional coordinates of each pixel in the region of interest for each image frame in the plurality of image frames;

determine a movement vector corresponding to each pixel in the region of interest between any two consequent image frames using a difference between the two dimensional coordinates of each pixel in the two consequent image frames;

determine a movement value for each pixel of an image frame by calculating an absolute value of the movement vector corresponding to each pixel; and determine the movement value for the image frame by calculating a sum of movement values of all pixels in the image frame.

17. The apparatus of claim 10, wherein the computer coded instructions further cause the apparatus to:

determine the movement value for all image frames in the plurality of image frames;

determine a maximum deviation in the movement value for all image frames in the plurality of image frames;

compare the maximum deviation in the movement value with a deviation movement threshold;

increase the deviation movement threshold when an ambient light intensity is lower than an ambient light threshold; and determine that human breathing is not detected when the maximum deviation in the movement value is less than the deviation movement threshold.

18. The apparatus of claim 10, wherein the computer coded instructions further cause the apparatus to:

capture a background image;

capture a foreground image;

determine a subtraction image using the background image and the foreground image;

remove noise from the subtraction image;

recognize a human image; and determine the region of interest as a region surrounding the human image.

19. A breath rate detection method comprising:

capturing, by an optical flow sensor, a plurality of image frames from a region of interest;

determining, by a computing device, a subset of image frames that include image frames having largest movement values in the plurality of image frames;

determining a first image frame in the subset of image frames and a last image frame in the subset of image frames; and determining, by the computing device, a breath rate using the first image frame and the last image frame in the subset of image frames and a rate of capturing the plurality of image frames.

20. The breath rate detection method of claim 19, further comprising:

determining, by the computing device, two dimensional coordinates of each pixel in the region of interest for each image frame in the plurality of image frames;

determining, by the computing device, a movement vector corresponding to each pixel in the region of interest between any two consequent image frames using a difference between the two dimensional coordinates of each pixel in the two consequent image frames;

determining, by the computing device, a movement value for each pixel of an image frame by calculating an absolute value of the movement vector corresponding to each pixel; and determining, by the computing device, a movement value for the image frame by calculating a sum of movement values of all pixels in the image frame.

* * * * *